United States Patent
Lin et al.

(10) Patent No.: US 10,849,533 B2
(45) Date of Patent: Dec. 1, 2020

(54) BLOOD VESSEL SCANNING SYSTEM AND METHOD

(71) Applicant: AU Optronics Corporation, Hsin-Chu (TW)

(72) Inventors: Chih-Hao Lin, Hsin-Chu (TW); Jhen-Yu You, Hsin-Chu (TW); Yi-Huan Liao, Hsin-Chu (TW); Chun Chang, Hsin-Chu (TW)

(73) Assignee: AU OPTRONICS CORPORATION, Hsin-Chu (TW)

( * ) Notice: Subject to any disclaimer, the term of this patent is extended or adjusted under 35 U.S.C. 154(b) by 196 days.

(21) Appl. No.: 15/953,753

(22) Filed: Apr. 16, 2018

(65) Prior Publication Data
US 2018/0317816 A1 Nov. 8, 2018

(30) Foreign Application Priority Data
May 5, 2017 (TW) .............................. 106115029 A

(51) Int. Cl.
| | | |
|---|---|---|
| *A61B 5/1171* | (2016.01) | |
| *A61B 5/00* | (2006.01) | |
| *A61B 5/01* | (2006.01) | |
| *G06T 7/00* | (2017.01) | |
| *A61B 5/0205* | (2006.01) | |

(52) U.S. Cl.
CPC .......... *A61B 5/1171* (2016.02); *A61B 5/0075* (2013.01); *A61B 5/0077* (2013.01); *A61B 5/01* (2013.01); *A61B 5/489* (2013.01); *A61B 5/6803* (2013.01); *A61B 5/746* (2013.01); *G06T 7/0014* (2013.01); *A61B 5/02055* (2013.01); *G06T 2207/30041* (2013.01)

(58) Field of Classification Search
CPC ... A61B 5/1171; A61B 5/0075; A61B 5/0077; A61B 5/01; A61B 5/489; A61B 5/746; A61B 5/02055; G06T 7/0014; G06T 2207/30041
See application file for complete search history.

(56) References Cited

U.S. PATENT DOCUMENTS

| | | |
|---|---|---|
| 2005/0071647 A1 | 3/2005 | Fujinuma et al. |
| 2005/0280108 A1 | 12/2005 | Kim |
| 2011/0186950 A1 | 8/2011 | Liu et al. |
| 2012/0104525 A1 | 5/2012 | Wu et al. |

FOREIGN PATENT DOCUMENTS

| | | |
|---|---|---|
| CN | 103618820 A | 3/2014 |
| TW | I259967 | 8/2006 |
| TW | 200708062 A | 2/2007 |

*Primary Examiner* — Paula J Stice
(74) *Attorney, Agent, or Firm* — WPAT, PC

(57) ABSTRACT

A blood vessel scanning system and method are provided, which are adapted for user identification. The blood vessel scanning system is implemented for a head-mounted image viewing device. The blood vessel scanning method comprises the following steps: determining whether a user is authorized or not according to the blood vessel scanning image of the user; if the user is an authorized user, the blood vessel scanning system adjusts lens degree of the head-mounted image viewing device according to the pre-stored visual information of the user.

8 Claims, 4 Drawing Sheets

BLOOD VESSEL SCANNING SYSTEM AND METHOD

BACKGROUND

Technical Field

The present disclosure relates to a blood vessel scanning system and method.

Related Art

In terms of the prior art, a blood vessel scanning product in the market photographs human tissues by using a light source and an infrared camera. Because hemoglobin in a blood vessel absorbs an infrared light, a dark-colored blood vessel outline image is obtained. To maintain accuracy of vein recognition, it is required that the photographing area is to be sufficiently large. However, traditional photographic equipment has a limited angle of view, and large-area photographing requires a long photographic distance. Therefore, in an instance that if a head-mounted device intends to photograph a human blood vessel by using the traditional photographic equipment to obtain a large-area photograph, the equipment needs to be kept at a certain distance from the human body. In this case, the entire head-mounted equipment will become heavy and causing a burden on a user.

SUMMARY

Embodiments of the present disclosure provide a blood vessel scanning system and method, where a photographed vein feature is selected for user identity authentication, so as to accurately determine whether an identity of a current user has any authorized privileges. In one embodiment, the system is configured in a head-mounted image viewing device, and the user is authenticated to use the image viewing device. In addition, in another embodiment, after it is determined that the user does have authorized privileges, the system can automatically adjust a lens degree of the head-mounted image viewing device according to visual acuity data of the user recorded in a database storage circuit, so that the user has better viewing experience.

A blood vessel scanning system, configured in a head-mounted image viewing device, wherein the system comprises a first microlens array, having a plurality of first lenses, and receiving at least two incident lights with different wavelengths, wherein at least two of the first lenses deviate in a first axial direction, and the first axial direction is the direction of the at least two incident lights after passing through the first microlens array; a second microlens array, having a plurality of second lenses; and a sensing component array, disposed between the first microlens array and the second microlens array; wherein each of first lenses is disposed corresponding to each of second lenses in the first axial direction.

In another embodiment further comprises the second microlens array; wherein after the at least two lights with different wavelengths focus on the sensing component array from the first microlens array, the at least two lights with different wavelengths diverge on each of the second lenses of the second microlens array, and then the second microlens array transmits lights in a specified position on a head of a user for obtaining a blood vessel scanning image and performing imaging in the sensing component array.

In another embodiment further comprises a light source, disposed adjacent to the first microlens array, for providing the at least two lights with different wavelengths, wherein the first microlens array is positioned between the light source and the sensing component array.

In another embodiment further comprises a light guiding plate, receiving the at least two lights with different wavelengths provided by the light source, for adjusting the at least two lights with different wavelengths to be incident into the first microlens array in parallel.

In another embodiment further comprises a processing unit, electrically coupled to the sensing component array, and for authenticating the user according to the blood vessel scanning image sensed by the sensing component array.

In another embodiment further comprises a database storage circuit, electrically coupled to the processing unit, wherein the database storage circuit stores first comparison information of at least one authorized user and a vein feature corresponding to at least one authorized user, and after obtaining the blood vessel scanning image sensed by the sensing component array, the processing unit compares the blood vessel scanning image with the first comparison information to determine whether the user is the at least one authorized user.

In another embodiment further comprises the database storage circuit further stores second comparison information that comprises a degree of myopia corresponding to the at least one authorized user, and after the processing unit determines that the user is the at least one authorized user, the processing unit adjusts a lens degree of the head-mounted image viewing device worn by the user according to the second comparison information.

In another embodiment further comprises the database storage circuit further stores a normal heart rate range and/or a normal body temperature range, after the processing unit obtains the blood vessel scanning image sensed by the sensing component array, the processing unit analyzes the blood vessel scanning image to calculate and to analyze a heart rate and a body temperature of the user, and when the heart rate and the body temperature are lower than or exceeding a predetermined normal heart rate range or a predetermined normal body temperature range, the processing unit sends a warning message.

A blood vessel scanning method, applicable to user identity authentication and implemented in a head-mounted image viewing device, wherein the blood vessel scanning method comprises providing first comparison information of a vein feature corresponding to at least one authorized user; comparing the blood vessel scanning image with the first comparison information to determine whether the to-be-authenticated user is the at least one authorized user after obtaining a blood vessel scanning image of a to-be-authenticated user; providing second comparison information of a degree of myopia of the at least one authorized user and the degree of myopia corresponding to the at least one authorized user; and adjusting a lens degree of the head-mounted image viewing device worn by the to-be-authenticated user according to the second comparison information after determining that the to-be-authenticated user is the at least one authorized user.

In another embodiment further comprises providing a predetermined normal heart rate range and a predetermined normal body temperature range; analyzing the blood vessel scanning image to calculate a heart rate and a body temperature of the user after obtaining the sensed blood vessel scanning image; determining whether the obtained heart rate and body temperature are lower than or exceeding the predetermined normal heart rate range or the predetermined normal body temperature range; and sending a warning message when the obtained heart rate and body temperature are lower than or exceeding the predetermined normal heart rate range or the predetermined normal body temperature range.

DETAILED DESCRIPTION

The following discloses a plurality of implementations of the present disclosure by using accompanying drawings. To specify the description, some details in practice are described below in the following descriptions. However, it should be understood that the details in practice should not be used to limit the present disclosure. In other words, in some implementations of the present disclosure, the details in practice are not necessary. In addition, to simplify the drawings, some conventional and consistently used structures and components are shown in a simple schematic manner.

Figure 1A:
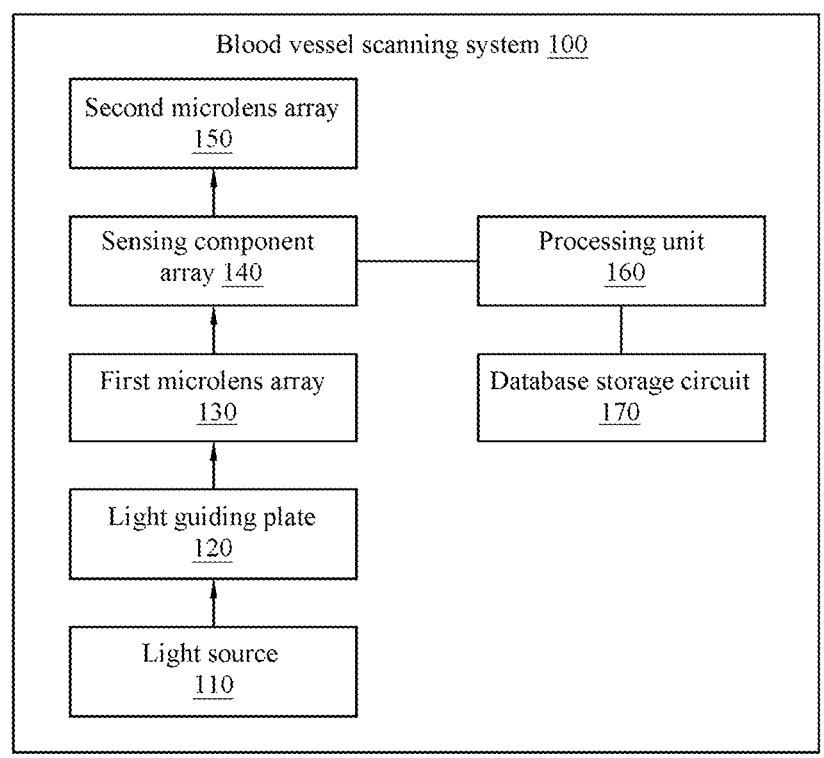
FIG. 1A and FIG. 1B are functional block diagrams of a blood vessel scanning system of a first implementation of the present disclosure.
Figure 1B:
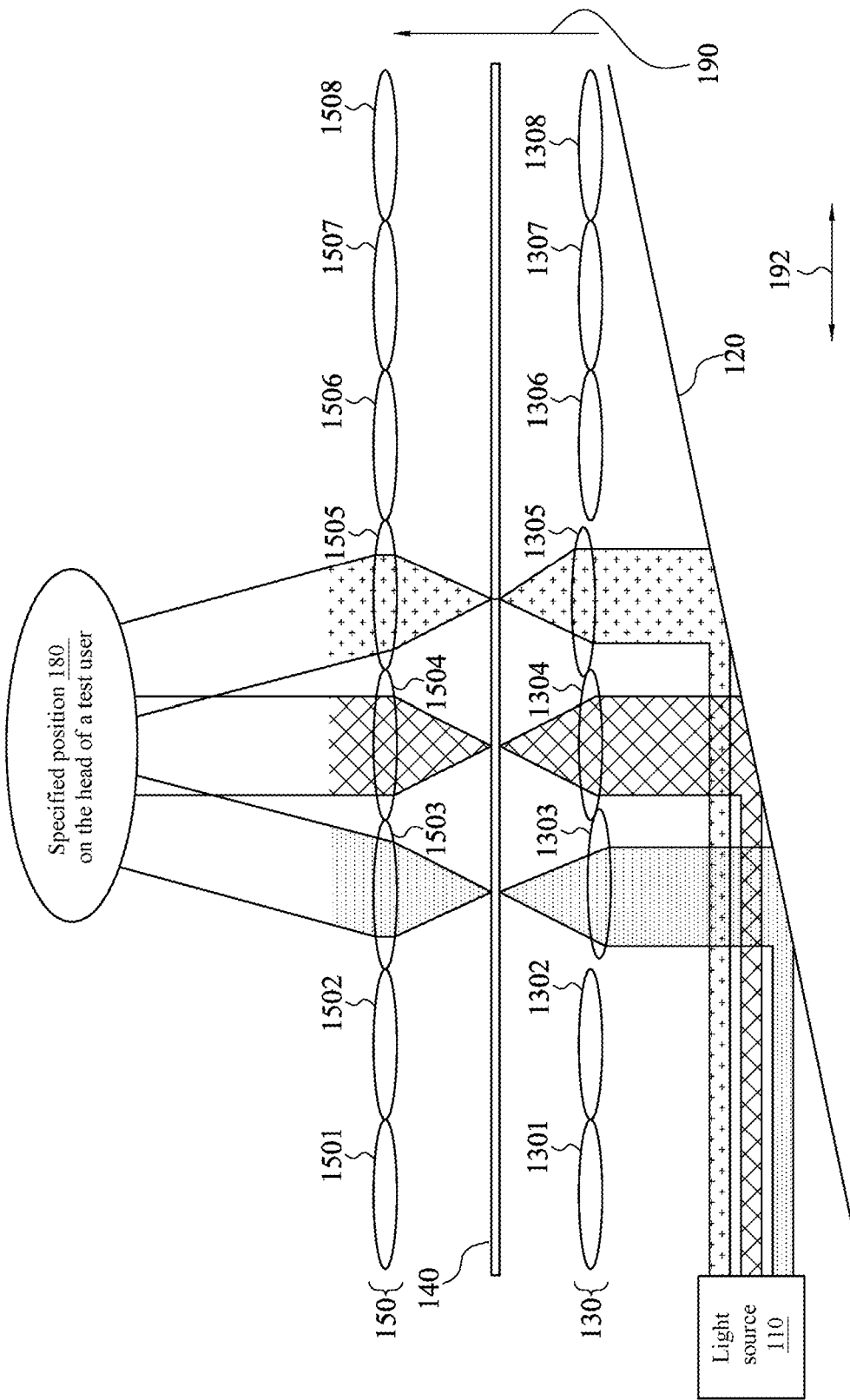
Figure 1C:
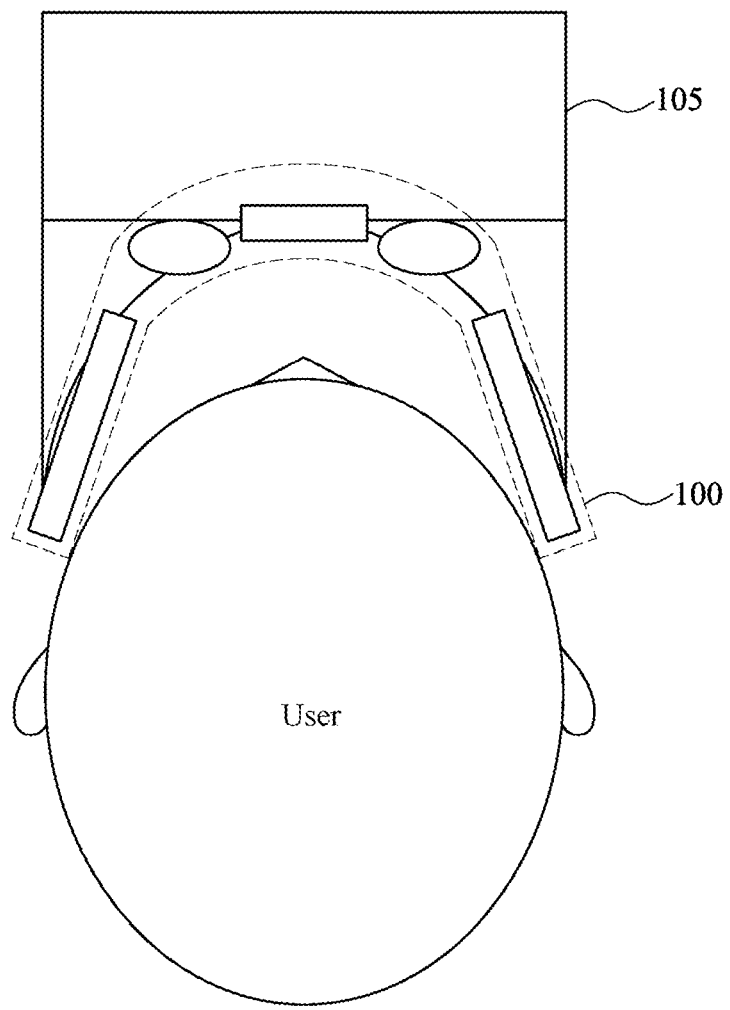
FIG. 1C is a configuration diagram of the blood vessel scanning system in a head-mounted image viewing device worn by a user of the first implementation of the present disclosure.

FIG. 1A and FIG. 1B are functional block diagrams of a blood vessel scanning system of a first implementation of the present disclosure. FIG. 1C is a configuration diagram of the blood vessel scanning system in a head-mounted image viewing device worn by a user of the first implementation of the present disclosure. The blood vessel scanning system 100 provided by the present disclosure includes: a light source 110, a light guiding plate 120, a first microlens array 130, a sensing component array 140, a second microlens array 150, a processing unit 160, and a database storage circuit 170. The blood vessel scanning system 100 is configured in a head-mounted image viewing device 105 (as shown in FIG. 1C). When a user (test user) uses the head-mounted image viewing device to watch videos, the blood vessel scanning system 100 provided by the present disclosure can scan a specified position 180 on the head of the user (test user) to obtain a blood vessel scanning image of the user (test user).

In the blood vessel scanning system 100, the first microlens array 130 has a plurality of first lenses, for example, the first lenses 1301, 1302, 1303, 1304, 1305, 1306, 1307, and 1308, where the first lenses 1301, 1302, 1303, 1304, 1305, 1306, 1307, and 1308 may be convex lenses. The light source 110 is disposed on one side of the first microlens array 130, and configured to provide at least two lights with different wavelengths. The light source 110 may be a light emitting diode. The light guiding plate 120 receives the at least two lights with different wavelengths provided by the light source 110, and the light guiding plate 120 adjusts the at least two lights with different wavelengths, so that the lights are incident into the first microlens array 130 roughly in parallel. The at least two lights with different wavelengths are infrared lights or visible lights. Due to the complex structure of the human body, different tissues or compositions absorb different wavelengths. In terms of this embodiment of the present disclosure, with respect to blood imaging within a blood vessel, because oxyhemoglobin in an artery and deoxyhemoglobin in a vein have different absorbance spectral characteristics, it needs to provide different wavelengths of light to get complete photographing.

The first microlens array 130 receives at least two incident lights with different wavelengths, where the at least two lights with different wavelengths are incident into each first lens in the first microlens array 130 one to one, and the first lenses 1303,1304, and 1305 deviate in the first axial direction 190, in other words, the first lenses 1303,1304, and 1305 are not at the same horizontal plane, as shown in FIG. 1B. The first axial direction 190 is the direction of the light after the light passes through the first microlens array 130, in which each of the incidental lights emerged into a respective focal point on the sensing component array 140 along the first axial direction 190. Further, each of the incidental lights, after emerging and passing the respective focal point on the sensing component array 140, diverges before reaching the second microlens array 150.

In more detail, an optical axis of the first microlens array 130 which is substantially parallel to the first axial direction and an optical axis of the second microlens array 150 are horizontally offset to adjust a refracted direction of the lights. In other words, the first microlens array 130 and the second microlens array 150 diverge in a horizontal direction so the lights can keep a distance from eyes, and prevent the eyes from being injured because of being directly illuminated by the lights. As shown in FIG. 1B, a horizontal deviation direction 192 is perpendicular to the first axial direction 190. In addition, because different wavelengths have different refractive indexes, the first microlens array 130 deviates vertically from the second microlens array 150 for compensation so that the lights with different wavelengths in different positions can converge in the same position.

The sensing component array 140 is disposed on another side of the first microlens array 130, and the light source 110 and the sensing component array 140 are at different side of the first microlens array 130. Each light of the at least two lights with different wavelengths is incident into each first lens 1301 to 1308 in the first microlens array 130 one to one, and then passes through and focuses on the sensing element array 140. After that, light passes the second microlens array 150 to the specified position 180 on the head of the user, and then reflects by the user and focuses on the sensing element array 140. It should be additionally noted that the "focusing on the sensing component array 140" also includes a case of focusing on the vicinity of the sensing component array 140 (or nearby the sensing component array 140), and is not limited to exactly focusing on the sensing component array 140.

The sensing component array 140 is disposed between the first microlens array 130 and the second microlens array 150. Each of the first lenses 1301 to 1308 in the first microlens array 130 is disposed corresponding to each of the second lenses 1501 to 1508 in the second microlens array 150 in the first axial direction 190.

The second microlens array 150 is formed by regularly arranging a plurality of second lenses, for example, second lenses 1501, 1502, 1503, 1504, 1505, 1506, 1507, and 1508. After the at least two lights with different wavelengths focus on and pass through the sensing component array 140, the at least two lights with different wavelengths diverge and reach to each of the second lenses of the second microlens array 150. The second microlens array 150 directs and converges the at least two lights towards a specified position 180 on the head of a user (test user) to obtain a blood vessel scanning image by scanning in the specified position on the head of the user (test user), and perform imaging in the sensing component array 140.

The processing unit 160 may be a central processing unit of a computer or a microcontroller of an electronic device. The processing unit 160 is coupled to the sensing component array 140, and determines whether the user (test user) is authorized or not according to the blood vessel scanning image sensed by the sensing component array 140.

Figure 2:
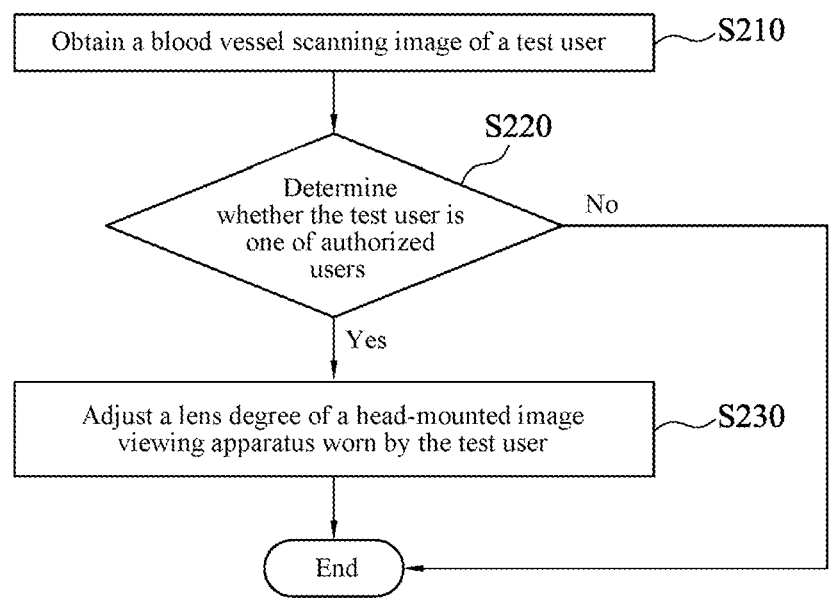
FIG. 2 is a flowchart of a blood vessel scanning method of the first implementation of the present disclosure.

FIG. 2 is a flowchart of a blood vessel scanning method of the first implementation of the present disclosure. A step of authenticating a user's identity and adjusting the connected device's operation in accordance of the corresponding data by means of blood vessel scanning is as follows: The database storage circuit 170 is electrically coupled to the processing unit 160, and the database storage circuit 170 stores first comparison information of at least one authorized user and a vein feature corresponding to the at least one authorized user. After obtaining the blood vessel scanning image of the user (step S210) sensed by the sensing component array 140, the processing unit 160 compares the obtained blood vessel scanning image with the first comparison information to determine whether the user (test user) is one of authorized users (step S220).

The database storage circuit 170 further stores second comparison information that includes a degree of myopia corresponding to each of the plurality of authorized users. When a result of the determining in step S220 is yes, which is after determining that the user (test user) is one of the authorized users, the processing unit 160 adjusts a lens degree of the head-mounted image viewing device, which is worn by the user (test user), according to the second comparison information (step S230).

In another embodiment of the present disclosure, the database storage circuit 170 further stores a normal heart rate range and/or a normal body temperature range, after the processing unit 160 obtains the blood vessel scanning image sensed by the sensing component array 140, the processing unit 160 analyzes the blood vessel scanning image, to calculate a heart rate and a body temperature of the user (test user); and the processing unit 160 analyzes the heart rate and the body temperature, and when the heart rate and the body temperature are lower than or exceed the normal heart rate range or the normal body temperature range, the processing unit 160 sends a warning message.

According to the blood vessel scanning system and method provided by the embodiments of the present disclosure, a photographed vein feature is selected for identity authentication, so as to accurately determine whether an identity of a current user has authorized privileges. In addition, after the user (test user) is authenticated and confirmed with the authorized privileges, the present disclosure can automatically adjust a lens degree of a head-mounted image viewing device according to visual acuity data of the user (test user) recorded in a database storage circuit, so that the user (test user) has better viewing experience.

Moreover, in the present disclosure, vein size change characteristics obtained by means of photographing can also be analyzed to calculate a heart rate and a body temperature of the user (test user), and when the heart rate and the body temperature do not fall within a normal range, a warning message is sent, to remind the user (test user).

Although the present disclosure has been disclosed by using a plurality of implementations, the implementations are not used to limit the present disclosure. A person skilled in the art can make various modifications and improvements without departing from the spirit and scope of the present disclosure. Therefore, the protection scope of the present disclosure should be subject to the scope defined by the appended claims.

What is claimed is:

1. A blood vessel scanning system, configured in a head-mounted image viewing device, comprises:
    a first microlens array, having a plurality of first lenses;
    a second microlens array, having a plurality of second lenses corresponding to the plurality of the first lenses;
    a sensing component array, disposed between the first microlens array and the second microlens array; and
    a light source for emitting a first light with a first wavelength and a second light with a second wavelength onto the first microlens array;
    wherein at least two of the first lenses in corresponding to the first light and the second light are distanced away from the sensing component with a first focusing distance and a second focusing distance, the first focusing distance is different from the second focusing distance, and the at least two of the first lenses accommodate focusing each of the first light and the second light into a first focus point and a second focus point on the sensing component array.

2. The blood vessel scanning system according to claim 1, wherein after the first light and the second light focus on and pass through the sensing component array, the first light and the second light diverge and reach the second microlens array, then the second microlens array transmits the first light and the second light to a specified position on a head of a user, and the sensing component array performs imaging upon receiving the first light and the second light reflected back from the specific area.

3. The blood vessel scanning system according to claim 2, further comprising:
    a processing unit, electrically coupled to the sensing component array, for authenticating the user according to a blood vessel scanning image imagined by the sensing component array.

4. The blood vessel scanning system according to claim 3, further comprising:
    a database storage circuit, electrically coupled to the processing unit, wherein the database storage circuit stores first comparison information comprising a vein feature of at least one authorized user, and after obtaining the blood vessel scanning image imagined by the sensing component array, the processing unit compares the blood vessel scanning image with the first comparison information to determine whether the user is the at least one authorized user.

5. The blood vessel scanning system according to claim 4, wherein the database storage circuit further stores second comparison information comprising a myopia information corresponding to the at least one authorized user, and after the processing unit determines that the user is the at least one authorized user, the processing unit adjusts a lens degree of the head-mounted image viewing device worn by the user according to the second comparison information.

6. The blood vessel scanning system according to claim 4, wherein the database storage circuit further stores a normal heart rate range or a normal body temperature range, upon obtaining the blood vessel scanning image imagined by the sensing component array, the processing unit analyzes the blood vessel scanning image to calculate and to analyze a heart rate or a body temperature of the user, and when the heart rate or the body temperature is lower than or exceeding a predetermined normal heart rate range or a predetermined normal body temperature range, the processing unit sends a warning message.

7. The blood vessel scanning system according to claim 1, wherein the first microlens array is positioned between the light source and the sensing component array.

8. The blood vessel scanning system according to claim 7, further comprising:
   a light guiding plate, for receiving the first light and the second light to be incident into the first microlens array in parallel.

* * * * *